US008815260B1

(12) United States Patent
Wu et al.

(10) Patent No.: US 8,815,260 B1
(45) Date of Patent: Aug. 26, 2014

(54) TREATMENT OF RESTENOSIS AND STENOSIS WITH DASATINIB

(75) Inventors: Jie Wu, Tampa, FL (US); Zhengming Chen, Tampa, FL (US); Kapil N. Bhalla, Tampa, FL (US)

(73) Assignees: University of South Florida, Tampa, FL (US); H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 13/273,731

(22) Filed: Oct. 14, 2011

Related U.S. Application Data

(62) Division of application No. 11/551,116, filed on Oct. 19, 2006, now abandoned.

(60) Provisional application No. 60/728,673, filed on Oct. 20, 2005.

(51) Int. Cl.
*A61K 9/00* (2006.01)

(52) U.S. Cl.
USPC ..................... 424/400; 514/252.19

(58) Field of Classification Search
CPC .................................... A61K 31/506
USPC ..................... 424/400; 514/252.19
See application file for complete search history.

(56) References Cited

U.S. PATENT DOCUMENTS

| | | | |
|---|---|---|---|
| 5,714,383 A | 2/1998 | Thompson | |
| 6,585,764 B2 | 7/2003 | Wright et al. | |
| 6,664,233 B1 * | 12/2003 | Rubinfeld | 514/19.4 |
| 7,055,237 B2 | 6/2006 | Thomas | |
| 7,279,175 B2 | 10/2007 | Chen et al. | |
| 7,482,034 B2 | 1/2009 | Boulais | |
| 2005/0214343 A1 | 9/2005 | Tremble et al. | |
| 2007/0078121 A1 | 4/2007 | Flynn et al. | |
| 2009/0233924 A1 * | 9/2009 | Ple et al. | 514/234.5 |

FOREIGN PATENT DOCUMENTS

| | | | |
|---|---|---|---|
| WO | 0062778 A1 | 10/2000 | |
| WO | WO 00 62778 | * 10/2000 | |
| WO | 03086497 A1 | 10/2003 | |
| WO | 2004085388 A2 | 10/2004 | |
| WO | 2006052810 A2 | 5/2006 | |

OTHER PUBLICATIONS

Lombardo et al ("Discovery of N-(2-Chloro-6-methyl-phenyl)-2-(6-(4-(2-hydroxyethyl)-piperazin-l-yl).2-methylpyrimidin-4-ylamino)thiazole-5-carboxamide (BMS-354825), a Dual Src/Abl Kinase Inhibitor with Potent Antitumor Activity in Preclinical Assays," J. Med. Chem. 2004, 47, 6658-6661).*
Chen et al. ("Potent Inhibition of Platelet-Derived Growth Factor-Induced Responses in Vascular Smooth Muscle Cells by BMS-354825 (Dasatinib)," Mol Pharmacol 69:1527-1533, 2006, published online before print Jan. 25, 2006).*
Zhan et al.. 2003. Role of JNK, p38, and ERK in Platelet-Derived Growth Factor-Induced Vascular Proliferation, Migration, and Gene Expression. Arterioscler. Thromb. Vasc. Biol. vol. 23. pp. 795-801.
Bristol Myers Squibb Company. 2006. Dasatinib (BMS-354825). Oncologic Drug Advisory Committee (ODAC) Briefing Document. NDA 21-986. pp. 1-66.
Bailey. 2002. Coronary Restenosis: A Review of Current Insights and Therapies. Catheterization and Cardiovascular Interventions. vol. 55. pp. 265-271.
Banai et al. 1998. PDGF-Receptor Tyrosine Kinase Blocker AG1295 Selectively Attenuates Smooth Muscle Cell Growth In Vitro and Reduces Neointimal Formation After Balloon Angioplasty in Swine. Circulation. vol. 97. pp. 1960-1969.
Bowman et al. 2001. Stat3-Mediated Myc Expression is Required for Src Transformation and PDGF-Induced Mitogenesis. PNAS. vol. 98. No. 13. pp. 7319-7324.
Buchdunger et al. 1996. Inhibition of the Abl Protein-Tyrosine Kinase in vitro and in vivo by a 2-Phenylaminopyrimidine Derivative. Cancer Res. vol. 56. pp. 100-104.
Burgess et al. 2005. Comparative Analysis of Two Clinically Active BCR-ABL Kinase Inhibitors Reveals the Role of Conformation-Specific Binding in Resistance. Proc. Natl. Acad. Sci. U. S. A. vol. 102. pp. 3395-3400.
Chen et al. 2006. Potent Inhibition of Platelet-Derived Growth Factor-Induced Responses in Vascular Smooth Muscle Cells by BMS-354825 (Dasatinib). vol. 69. No. 5. pp. 1527-1533.
Cunnick et al. 2001. Phosphotyrosines 627 and 659 of Gab1 Constitute a Bisphosphoryl Tyrosine-Based Activation Motif (BTAM) Conferring Binding and Activation of SHP2. J. Biol. Chem. vol. 276. pp. 24380-24387.
Cunnick et al. 2002. Regulation of the Mitogen-Activated Protein Kinase Signaling Pathway by SHP2. J. Biol. Chem. vol. 277. pp. 9498-9504.
Dahring et al. 1997. Inhibition of Growth Factor-Mediated Tyrosine Phosphorylation in Vascular Smooth Muscle by PD 089828, a New Synthetic Protein Tyrosine Kinase Inhibitor. The Journal of Pharmacology and Experimental Therapeutics. vol. 281. No. 3. pp. 1446-1456.
Dangas et al. 2002. Restenosis: Repeat Narrowing of a Coronary Artery: Prevention and Treatment. Circulation. vol. 105. pp. 2586-2587.
Deininger et al. 2005. The Development of Imatinib as a Therapeutic Agent for Chronic Myeloid Leukemia. Blood. vol. 105. No. 7. pp. 2640-2653.
Dorsey et al. 2000. The Pyrido[2,3-d]pyrimidine Derivative PD180970 Inhibits p210(Bcr-Abl) Tyrosine Kinase and Induces Apoptosis of K562 Leukemic Cells. Cancer Res. vol. 60. pp. 3127-3131.

(Continued)

*Primary Examiner* — Suzanne Ziska
(74) *Attorney, Agent, or Firm* — Robert J. Varkonyi; Smith & Hopen, P.A.

(57) ABSTRACT

A method for treating or inhibiting artery obstructive disease, such as restenosis after angioplasty and stenting procedures and stenosis after coronary artery bypass surgery, in a subject by administering to the subject a therapeutically effective amount of dasatinib or a derivative thereof. Also provided are drug-eluting medical devices, including stents, having a therapeutically effective amount of dasatinib.

19 Claims, 8 Drawing Sheets

(56) References Cited

OTHER PUBLICATIONS

Druker et al. 1996. Effects of a Selective Inhibitor of the Abl Tyrosine Kinase on the Growth of Bcr-Abl Positive Cells. Nat. Med. vol. 2. No. 5. pp. 561-566.
Ferns et al. 1991. Inhibition of Neointimal Smooth Muscle Accumulation After Angioplasty by an Antibody to PDGF. Science. vol. 253. pp. 1129-1132.
Fishbein et al. 2000. Local Delivery of Platelet-Derived Growth Factor Receptor-Specific Tyrphostin Inhibits Neointimal Formation in Rats. Arterioscler Thromb. Vasc. Biol. vol. 20. pp. 667-676.
Graf et al. 1997. Mitogen-Activated Protein Kinase Activation is Involved in Platelet-Derived Growth Factor-Directed Migration by Vascular Smooth Muscle Cells. Hypertension. vol. 29. pp. 334-339.
Heldin et al. 1999. Mechanism of Action and In Vivo Role of Platelet-Derived Growth Factor. Physiol. Rev. vol. 79. No. 4. pp. 1283-1316.
Huron et al. 2003. A Novel Pyridopyrimidine Inhibitor of Abl Kinase is a Picomolar Inhibitor of Bcr-abl-driven K562 Cells and is Effective Against STI571-Resistant Bcr-abl Mutants. Clin. Cancer Res. vol. 9. pp. 1267-1273.
Kallin et al. 2004. Gab1 Contributes to Cytoskeletal Reorganization and Chemotaxis in Response to Platelet-Derived Growth Factor. The Journal of Biological Chemistry. vol. 279. No. 17. pp. 17897-17904.
Kim et al. 2005. Luteolin Prevents PDGF-BB-Induced Proliferation of Vascular Smooth Muscle Cells by Inhibition of PDGF Beta-Receptor Phosphorylation. Biochem. Pharmacol. vol. 69. pp. 1715-1721.
Lahaye et al. 2005. Response and Resistance in 300 Patients with BCR-ABL-Positive Leukemias Treated with Imatinib in a Single Center: a 4.5-Year Follow-Up. Cancer. vol. 103. pp. 1659-1669.
Levitzki. 2005. PDGF Receptor Kinase Inhibitors for the Treatment of Restenosis. Cardiovasc. Res. vol. 65. pp. 581-586.
Li et al. 2009. Characterization of Dasatinib and its Structural Analogs as CYP3A4 Mechanism Based Inactivators and the Proposed Bio-Activation Pathways. American Society for Pharmacology and Experimental Therapeutics. pp. 1-33.
Logrono et al. 2004. Recent Advances in Cell Biology, Diagnosis, and Therapy of Gastrointestinal Stromal Tumor (GIST). Cancer Biol. Ther. vol. 3.No. 3. pp. 251-258.
Lombardo et al. (2004) Discovery of N-(2-chloro-6-methyl-phenyl)-2-(6-(4-(2-hydroxyethyl)- piperazin-1-yl)-2-methylpyrimidin-4-ylamino)thiazole-5-carboxamide (BMS-354825), a Dual Src/Abl Kinase Inhibitor with Potent Antitumor Activity in Preclinical Assays. J. Med. Chem. vol. 47. pp. 6658-6661.
Michaels et al. 2002) Angioplasty Versus Bypass Surgery for Coronary Artery Disease. Circulation. vol. 106. pp. e187-e190.
Myllarniemi et al. 1999. Selective Tyrosine Kinase Inhibitor for the Platelet-Derived Growth Factor Receptor in Vitro Inhibits Smooth Muscle Cell Proliferation After Reinjury of Arterial Intima in Vivo. Cardiovasc. Drugs Ther. vol. 13. pp. 159-168.
Neeli et al. 2004. An Essential Role of the Jak-2/STAT-3/cytosolic phospholipase A(2) Axis in Platelet-Derived Growth Factor BB-Induced Vascular Smooth Muscle Cell Motility. J. Biol. Chem. vol. 279. No. 44. pp. 46122-46128.
O'Hare et al. 2005. In Vitro Activity of Bcr-Abl Inhibitors AMN107 and BMS-354825 Against Clinically Relevant Imatinib-Resistant Abl Kinase Domain Mutants. Cancer Res. vol. 65. No. 11. pp. 4500-4505.
Panek et al. 1997. In Vitro Pharmacological Characterization of PD 166285, a New Nanomolar Potent and Broadly Active Protein Tyrosine Kinase Inhibitor. The Journal of Pharmacology and Experimental Therapeutics. vol. 283. No. 3. pp. 1433-1444.
Raines. 2004. PDGF and Cardiovascular Disease. Cytokine Growth Factor Rev. vol. 15. pp. 237-254.
Rao et al. 1997. The A10 Cell Line: a Model for Neonatal, Neointimal, or Differentiated Vascular Smooth Muscle Cells? Cardiovasc. Res. vol. 36. pp. 118-126.
Ren et al. 2004. Roles of Gab1 and SHP2 in Paxillin Tyrosine Dephosphorylation and Src Activation in Response to Epidermal Growth Factor. J. Biol. Chem. vol. 279. No. 9. pp. 8497-8505.
Ren et al. 2003. Simultaneous Suppression of Erk and Akt/Pkb Activation by a Gab1 Pleckstrin Homology (PH) Domain Decoy. Anticancer Res vol. 23. pp. 3231-3236.
Sanz-Gonzalez et al. 2004. Role of E2F and ERK1/2 in STI571-Mediated Smooth Muscle Cell Growth Arrest and Cyclin A Transcriptional Repression. Biochem. Biophys. Res. Commun. vol. 317. pp. 972-979.
Shah et al. 2004. Overriding Imatinib Resistance with a Novel ABL Kinase Inhibitor. Science. vol. 305. pp. 399-401.
Shibata et al. (2003) Inhibition of STAT3 Prevents Neointima Formation by Inhibiting Proliferation and Promoting Apoptosis of Neointimal Smooth Muscle Cells. Hum. Gene Ther. vol. 14. No. 601-610.
Sihvola et al. 2003. Platelet-Derived Growth Factor Receptor Inhibition Reduces Allograft Arteriosclerosis of Heart and Aorta in Cholesterol-Fed Rabbits. Transplantation. vol. 75. No. 3. pp. 334-339.
Bristol-Myers Squibb Company. 2009. Sprycel. Highlights of Prescribing Information.
Vantler et al. 2005. Systematic Evaluation of Anti-Apoptotic Growth Factor Signaling in Vascular Smooth Muscle Cells. Only Phosphatidylinositol 3'-Kinase is Important. J. Biol. Chem. vol. 280. No. 14. pp. 14168-14176.
Waltenberger et al. 1999. A Dual Inhibitor of Platelet-Derived Growth Factor Beta-Receptor and Src Kinase Activity Potently Interferes with Motogenic and Mitogenic Responses to PDGF in Vascular Smooth Muscle Cells: A Novel Candidate for Prevention of Vascular Remodeling. Circ. Res. vol. 85. pp. 12-22.
Wang et al. 2000. Activation of Stat3 Preassembled with Platelet-Derived Growth Factor Beta Receptors Requires Src Kinase Activity. Oncogene. vol. 19. pp. 2075-2085.
Weber et al. 2004. Phosphoinositide-Dependent Kinase 1 and p21-Activated Protein Kinase Mediate Reactive Oxygen Species-Dependent Regulation of Platelet-Derived Growth Factor-Induced Smooth Muscle Cell Migration. Circ. Res. vol. 94. pp. 1219-1226.
Medpedia. 2010. Dasatinib. Accessed http://wiki.medpedia.com/Dasatinib on Apr. 28, 2010.
Wisniewski et al. 2002. Characterization of Potent Inhibitors of the Bcr-Abl and the c-Kit Receptor Tyrosine Kinases. Cancer Res. vol. 62. pp. 4244-4255.
Huang et al. 2002. Insulin and Local Growth Factor PDGF Induce Intimal Hyperplasia in Bypass Graft Culture Models of Saphenous Vein and Internal Mammary Artery. European Journal of Cardiothoracic Surgery. vol. 21. pp. 1002-1008.
Zohlnhöfer, et al.; "A Randomized, Double-Blind, Placebo-Controlled Trial on Restenosis Prevention by the Receptor Tyrosine Kinase Inhibitor Imatinib"; Journal of the American College of Cardiology; vol. 46, No. 11, pp. 1999-2003; 2005.
Bristol-Myers Squibb Company; "Sprycel-Dasatinib Product Sheet"; pp. 1-8; Nov. 2008.
Hinz, et al.; "Pharmacokinetics of the in Vivo and in Vitro Conversion of 9-Nitro-20(S)-camptothecin to 9-Amino-20(S)-camptothecin in Humans, Dogs and Mice"; Cancer Research; vol. 54, pp. 3096-3100; Jun. 15, 1994.
Hacker, et al.; "Platelet-Derived Growth Factor Receptor Antagonist STI571 (Imatinib Mesylate) Inhibits Human Vascular Smooth Muscle Proliferation and Migration In Vitro But Not In Vivo"; The Journal of Invasive Cardiology; vol. 19, No. 6, pp. 269-274, Jun. 2007.
Judah Folkman and Yuen Shing, Angiogenesis. Minireview. The Journal of Biological Chemistry. vol. 267, No. 16, Issue of Jun. 5, pp. 10931-10934, 1992.
Angiogenesis Inhibitors—National Cancer Institute. Fact Sheet; Reveiwed Oct. 7, 2011. pp. 1-4. http://www.cancer.gov/cancertopics/factsheet/therapy/angiogenesis-inhibitors. Accessed on Jul. 27, 2012.
Neil P. Shah, et al., Multiple BCR-ABL kinase domain mutations confer polyclonal resistance to the tyrosine kinase inhibitor imatinib (STI571) in chronic phase and blast crisis chronic myeloid leukemia. Cancer Cell, Aug. 2002, vol. 2. pp. 117-125.
Lombardo LJ, et al., Discovery of N-(2-chloro-6-methyl-phenyl)-2-(6-(4-(4-hydroxyethyl)-piperazin-1-yl)-2-methylpyrimidin-4-ylamino) thiazole-5-carboxamide (BMS-354825), a dual Src/Abl

(56) References Cited

OTHER PUBLICATIONS kinase inhibitor with potent natitumor activity in preclinical assyas. http://www.ncbi.nlm.nih.gov/pubmed/15615512. Accessed on Jul. 25, 2012.

Chen, Z. et al. Potent Inhibition of Platelet-Derived Growth Factor-Induced Responses in Vascular Smooth Muscle Cells by BMS-354825 (dasatinib). Mol Pharmacol. May 2006; 69(5): 1527-33. Epub Jan. 25, 2006, http://www.ncbi.nlm.nih.gov/pubmed/16436588 (last accessed Jan. 20, 2014).

* cited by examiner

TREATMENT OF RESTENOSIS AND STENOSIS WITH DASATINIB

CROSS REFERENCE TO RELATED APPLICATIONS

This application is a divisional application of U.S. Nonprovisional application Ser. No. 11/551,116, entitled "Treatment of Restenosis and Stenosis with Dasatinib", filed on Oct. 19, 2006 now abandoned, which claims priority to U.S. Provisional Patent Application 60/728,673, entitled, "Potent Inhibition of Platelet-Derived Growth Factor-Induced Responses in Vascular Smooth Muscle Cells By BMS-354825", filed Oct. 20, 2005, the contents of which are herein incorporated by reference.

FIELD OF INVENTION

This invention relates to prevention and treatment of artery obstructive diseases. More specifically, this invention relates to methods for treating or preventing restenosis and stenosis in humans using dasatinib.

BACKGROUND OF THE INVENTION

Balloon angioplasty and stenting (percutaneous coronary interventions with or without the use of stents) are widely used procedures for coronary artery disease. Unfortunately, renarrowing (restenosis) of the dilated artery occurs in 25-40% of patients within six months after these procedures, which requires repeat angioplasty or bypass surgery (Dangas and Kuepper, 2002; Michaels and Chatterjee, 2002). Therefore, restenosis represents a major problem limiting the long-term efficacy of these revascularization therapies. Moreover, following coronary artery bypass surgery, narrowing (stenosis) of the transplanted artery can also occur that necessitates further medical treatments.

Abnormal migration and proliferation of VSMCs are critical events in the pathogenesis of artery obstructive diseases such as restenosis (Bailey, 2002; Levitzki, 2005; Sanz-Gonzalez et al., 2004). While several growth factors and cytokines are involved in the development of restenosis, many lines of evidence have indicated that PDGF plays a prominent role in the pathogenesis of restenosis. PDGF is the most potent mitogen and motogen for VSMCs (Heldin and Westermark, 1999). PDGF is present at sites of vascular injury from activated platelets, monocytes, and cells of the artery wall (Raines, 2004). Expression of exogenous PDGF in animal arteries can induce intimal thickening through stimulation of VSMC proliferation and migration and synthesis of extracellular matrix (Pompili et al., 1995). Importantly, inhibition of PDGF as well as PDGFR by immunological, molecular biological, and pharmacological methods can suppress development of restenotic lesions in animal models (Ferns et al., 1991; Levitzki, 2005; Myllarniemi et al., 1999; Sirois et al., 1997).

Imatinib (Gleevec, STI571, CGP57148B) is the first protein tyrosine kinase inhibitor that has been successfully developed into a targeted therapy drug. It is currently used to treat chronic myeloid leukemia (CML) and gastrointestinal stromal tumor based on inhibition of Bcr-Abl and c-Kit protein tyrosine kinases, respectively (Deininger et al., 2005; Logrono et al., 2004). Besides Bcr-Abl and c-Kit, imatinib also inhibits PDGFR tyrosine kinase (Buchdunger et al., 1996; Druker et al., 1996). Experiments in animals have shown that imatinib inhibits restenosis after balloon angioplasty and stenosis after allograft (Myllarniemi et al., 1999; Sihvola et al., 2003). Inhibition of PDGFR by imatinib, however, requires micromolar concentrations in cell-based assays (Buchdunger et al., 1996; Sanz-Gonzalez et al., 2004).

An additional approach to reducing restenosis is through the use of stents. A stent is a wire mesh tube used to prop open an artery after angioplasty. Restenosis is found to be less common in stented arteries.

SUMMARY OF INVENTION

The present invention provides a novel method for treating or inhibiting artery obstructive disease, such as restenosis (typically encountered after angioplasty and stenting procedures) and stenosis (typically encountered after coronary artery bypass surgery), in a subject by administering to the subject a therapeutically effective amount of dasatinib or a derivative thereof.

In one aspect the present invention provides a method of treating or inhibiting restenosis or stenosis in a patient comprising administering to a patient in need of such treatment a composition comprising dasatinib or a pharmaceutically acceptable derivative thereof in an amount effective to treat or inhibit restenosis or stenosis. In certain advantageous embodiments the dasatinib is administered orally. In further advantageous embodiments the dasatinib is administered with one or more additional therapeutic agents. The one or more additional therapeutic agents can include antiplatelet agents, antimigratory agents, antifibrotic agents, antiproliferatives, antiinflammatories and combinations thereof. In a particularly advantageous embodiment the one or more additional therapeutic agents is sirolimus or paclitaxel.

In a second aspect the present invention provides a method of treating or inhibiting artery obstructive disease in a patient comprising administering to a patient in need of such treatment a composition comprising dasatinib or a pharmaceutically acceptable derivative or analog thereof in an amount effective to treat artery obstructive disease. In a third aspect the present invention provides a method of treating or inhibiting restenosis or stenosis in a patient comprising administering to a patient in need of such treatment a composition comprising a dual Src/PDGFR inhibitor. In a fourth aspect the present invention provides a method of treating or inhibiting artery obstructive disease in a patient comprising administering to a patient in need of such treatment a composition comprising a dual Src/PDGFR inhibitor. In further advantageous embodiments the dual Src/PDGFR inhibitor is administered with one or more additional therapeutic agents. The one or more additional therapeutic agents can include antiplatelet agents, antimigratory agents, antifibrotic agents, antiproliferatives, antiinflammatories and combinations thereof. In a fifth aspect the present invention provides a method of treating restenosis in a patient comprising administering to a patient in need of such treatment a composition comprising a nanomolar concentration of a PDGFR tyrosine kinase inhibitor.

In still another aspect the present invention provides a stent having a coating comprising dasatinib or a pharmaceutically acceptable derivative thereof. In an advantageous embodiment the stent at least one additional therapeutic agent coated thereon. The additional therapeutic agent can be selected from the group consisting of antiplatelet agents, antimigratory agents, antifibrotic agents, antiproliferatives, antiinflammatories and combinations thereof. In a particularly advantageous embodiment the additional therapeutic agent is sirolimus or paclitaxel.

In still another aspect the present invention provides a medical device comprising an implantable device having a coating comprising a therapeutic amount of dasatinib or a pharmaceutically acceptable derivative thereof for the site-specific, controlled release of the therapeutic amount. The device can include at least one additional therapeutic agent coated thereon. The additional therapeutic agent can include antiplatelet agents, antimigratory agents, antifibrotic agents, antiproliferatives, antiinflammatories and combinations thereof.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
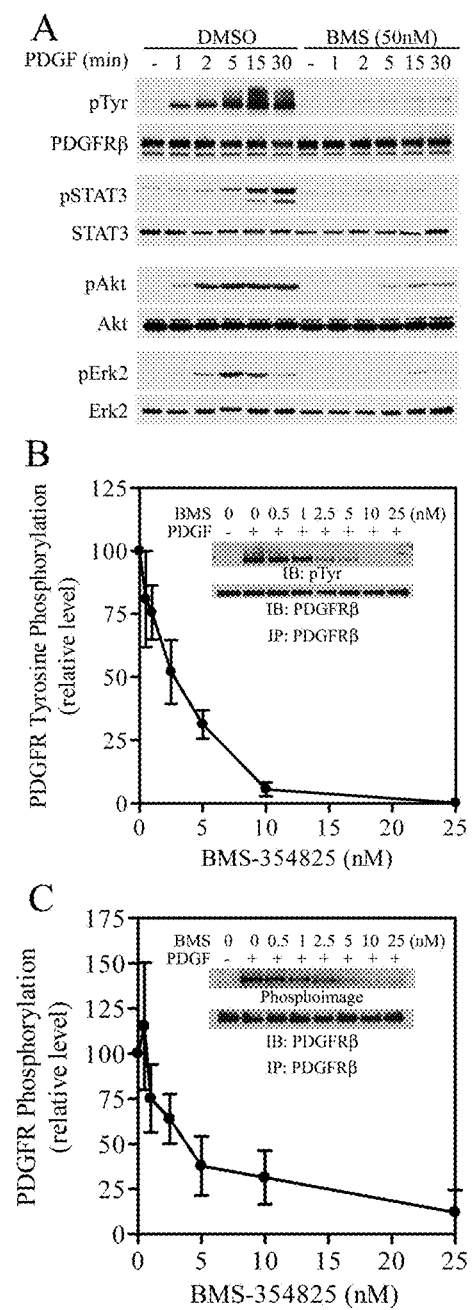
FIG. 1 shows the effect of BMS-354825 (Dasatinib, SPRYCEL) on PDGF-stimulated activation of PDGFR, STAT3, Akt, and Erk in rat A10 VSMCs. (A) Time-dependent activation of PDGFR, STAT3, Akt, and Erk2 in A10 cells. Subconfluent A10 cells were serum starved for 18 h, pre-incubated with BMS-354825 (50 nM, 20 min) or DMSO (–) for 20 min, and then treated with PDGF-BB (5 ng/ml) for the indicated time. Cell lysate supernatants (20 μg/each) were analyzed by immunoblotting with antibodies to phosphotyrosine, phospho-STAT3, phospho-Akt, phospho-Erk1/2, PDGFRβ, total STAT3, total Aid, and total Erk1/2. (B) Serum-starved A10 cells were pre-treated with indicated concentrations of BMS-354825 and then stimulated with PDGF (5 ng/ml, 5 min) PDGFβ was immunoprecipitated from cell lysates. The immunoprecipitates were analyzed by antibodies to phosphotyrosine (pTyr) and PDGFβ (inset). The relative pTyr signal intensities were compared. The graph represents data from three experiments, one of which was performed in duplicate (n=4). Each data point in the graph represents mean±SEM (this applies to all subsequent graphs). (C) BMS-354825 inhibited PDGFR tyrosine kinase activity in vitro. PDGFR was immunoprecipitated from A10 cells stimulated with PDGF-BB (5 ng/ml, 5 min) A portion of each immunoprecipitate (5/7) was used for in vitro kinase assay in the presence of BMS-354825 at the indicated concentrations. The remaining immunoprecipitates were used for immunoblotting analysis with anti-PDGFRβ antibody (inset). The graph is derived from three experiments.

Abnormal migration and proliferation of vascular smooth muscle cells (VSMCs) are key events in the pathogenesis of restenosis that undermine the long-term benefit of widely performed balloon angioplasty and stenting procedures. Platelet-derived growth factor (PDGF) is a potent mitogen and motogen for VSMCs and is known to play a prominent role in the intimal accumulation of smooth muscle cells. In this study, we analyzed the effects of a novel protein tyrosine kinase inhibitor, BMS-354825 (dasatinib), on PDGF-stimulated VSMCs. BMS-354825 is an orally bioavailable dual Src/Bcr-Abl tyrosine kinase inhibitor currently undergoing clinical trials in cancer patients. We found that BMS-354825 inhibited PDGF-stimulated activation of PDGF receptor (PDGFR), STAT3, Akt, and Erk2 in rat A10 VSMCs and in primary cultures of human aortic smooth muscle cells (AoSMCs) at low nanomolar concentrations. The 50% inhibition of the PDGFRβ tyrosine kinase activity in vitro by BMS-354825 was observed at 4 nM. Direct comparison of BMS-354825 and another PDGFR inhibitor, imatinib (Gleevec, STI571), in VSMCs indicated that BMS-354825 is 67-fold more potent than imatinib in inhibition of PDGFR activation. BMS-354825 also inhibited Src tyrosine kinase in A10 cells. At the cell level, PDGF stimulated migration and proliferation of A10 cells and human AoSMCs, both of which were inhibited by BMS-354825 in a concentration dependent manner in the low nanomolar range. These results suggest that BMS-354825 is a potent inhibitor of PDGF-stimulated VSMC activities and a potential agent for the development of a new therapy for vascular obstructive diseases such as restenosis.

Dasatinib (BMS-354825, SPRYCEL) has been approved by the U.S. FDA (Jun. 28, 2006) for (1) treatment of adults with all phases of chronic myeloid leukemia (CML) with resistance or intolerance to prior therapy, including Gleevec (imatinib mesylate) and (2) treatment of adults with Philadelphia chromosome-positive acute lymphoblastic leukemia (Ph+ALL) with resistance or intolerance to prior therapy. We demonstrate here that it is very effective in inhibiting PDGF-stimulated VSMC migration and proliferation. VSMC migration and proliferation are critical events in the development of restenosis and stenosis, which are the major problems for the long-term efficacy of the widely performed angioplasty and stenting procedures and the coronary artery bypass operation for coronary artery disease. Thus, in addition to being a promising anti-cancer drug, BMS-354825 is a potential novel therapeutic agent for cardiovascular diseases involving abnormal VSMC activities such as restenosis and stenosis.

Dasatinib is the generic name for the compound N-(2-chloro-6-methylphenyl)-2-[[6-[4-[(2-hydroxyethyl)-1-piperazinyl]-2-methyl-4-pyrimidinyl]amino]-5-thiazolecarboxamide, monohydrate, also known as BMS-354825 and SPRYCEL, of the following formula I:

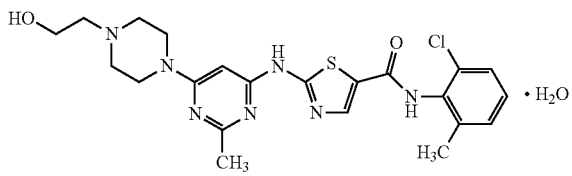

(I)

The compounds of Formula I may be prepared by the procedures described in PCT publication, WO 00/62778 published Oct. 26, 2000. The compound of formula I may be administered as described therein or as described in WO2004/085388, or as further described below with respect to the treatment of restenosis/artery obstructive diseases.

Amounts of dasatinib (BMS-354825) effective to treat restenosis would broadly range between about 10 mg. and about 150 mg. per day, more generally range between about 35 mg. and about 140 mg. per day, and preferably between about 70 mg. and about 140 mg. per day (administered orally twice a day). The rationale for the preferred dose range is based upon BMS-354825 dosing for CML and the clinical pharmacology data presented in "Dasatinib (BMS-354825) Oncologic Drug Advisory Committee (ODAC) briefing document, NDA-21-986, in which the Cmax was between approximately 60-120 nM. Whereas treatment of CML require high doses of dasatinib (BMS-354825) in order for the drug to reach its targets, such as the bone marrow, the arteries should be effectively targeted with lower doses because of relatively high concentrations of drug in the bloodstream following its oral administration and absorption in the intestine. These lower BMS-354825 doses should minimize the risk of toxicity. It is further envisioned that BMS-354825 may be administered either alone or in conjunction with therapies aimed at blocking vascular smooth muscle cell proliferation and inflammation such as sirolimus-eluting stent and a paclitaxel-eluting stent.

The present invention also encompasses a pharmaceutical composition useful in the treatment of artery obstructive diseases, particularly restenosis, comprising the administration of a therapeutically effective amount of the compound of the present invention, either alone or in combination with other compounds useful in the treatment of artery obstructive diseases, with or without pharmaceutically acceptable carriers or diluents. The compositions of the present invention may further comprise one or more pharmaceutically acceptable additional ingredient(s) such as alum, stabilizers, antimicrobial agents, buffers, coloring agents, flavoring agents, adjuvants, and the like. The compositions of the present invention may be administered orally or parenterally including the intravenous, intramuscular, intraperitoneal, subcutaneous, rectal and topical routes of administration.

The compositions of the present invention may be delivered as a coating, or otherwise integral to, an implantable medical device such as stents. Coated implantable devices may be prepared as described in U.S. Pat. No. 6,585,764 to Wright et al. and US2005/0214343A1 to Tremble et al.

For oral use, the compositions of this invention may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added.

In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

For preparing suppositories according to the invention, a low melting wax such as a mixture of fatty acid glycerides or cocoa butter is first melted, and the active ingredient is dispersed homogeneously in the wax, for example by stirring. The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The composition described herein may also be delivered transdermally. The transdermal compositions can take the form of creams, lotions, aerosols and/or emulsions and can be included in a transdermal patch of the matrix or reservoir type as are conventional in the art for this purpose.

The combinations of the present invention may also be used in conjunction with other well known therapies that are selected for their particular usefulness against the condition that is being treated.

The effective amount of the compounds of the combination of the present invention may be determined by one of ordinary skill in the art, and includes exemplary dosage amounts for an adult human of from about 0.1 to 2 mg/kg of body weight of active compound per day, preferably at a dose from 0.1 to 2 mg/kg of body weight which may be administered in a single dose or in the form of individual divided doses, such as from 1 to 2 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Subjects for treatment include animals, most preferably mammalian species such as humans, and domestic animals such as dogs, cats and the like, subject to protein tyrosine kinase-associated disorders.

When administered intravenously, the compounds of the combination of the present invention, are preferably administered using the formulations of the invention.

As discussed above, compounds of the combination of the present invention, can be administered orally, intravenously, or both or as drug-eluting stents. In particular, the methods of the invention encompass dosing protocols such as once a day for 2 to 10 days, every 3 to 9 days, every 4 to 8 days and every 5 days. In one embodiment there is a period of 3 days to 5 weeks, 4 days to 4 weeks, 5 days to 3 weeks, and 1 week to 2 weeks, in between cycles where there is no treatment. In another embodiment the compounds of the combination of the present invention can be administered orally, intravenously, or both, once a day for 3 days, with a period of 1 week to 3 weeks in between cycles where there is no treatment. In yet another embodiment the compounds of the combination of the present invention can be administered orally, intravenously, or both, once a day for 5 days, with a period of 1 week to 3 weeks in between cycles where there is no treatment.

Because of local delivery afforded by the release of the compound from a drug-eluting stent, the locally delivered dasatinib will likely result in less toxicity. Therefore, higher doses would be appropriate, such as 50-200 nM. (based upon dasatinib Mr=488. 50 nM=~25 ng/ml, 100 nM=~50 ng/ml, 200 nM=100 ng/ml, in the oral delivery route, 140 mg/day, Cmax is about 30-60 ng/ml).

In one embodiment the treatment cycle for administration of the compounds of the combination of the present invention, is once daily for 5 consecutive days and the period between treatment cycles is from 2 to 10 days, or one week. In one embodiment, a combination of the compound of the present invention, is administered once daily for 5 consecutive days, followed by 2 days when there is no treatment.

The compounds of the combination of the present invention can also be administered orally, intravenously, or both, once every 1 to 10 weeks, every 2 to 8 weeks, every 3 to 6 weeks, and every 3 weeks.

In another embodiment of the invention, the compound of formula I may be administered in a dose of 15-200 mg twice a day, or 30-100 mg twice a day. In one embodiment, the compound of formula I may be administered at 70 mg twice a day. In another embodiment, the compound of formula I may be administered in a dose of 50-300 mg once a day, or 100-200 mg once a day.

Alternatively, the compound of formula I may be administered in a dose of 70-150 mg twice a day or 140-250 mg once a day. Alternatively, the compound of formula I may be administered at 10, 15, 20, 25, 30, 35, 40, 50, 60, 70, 80, 90, 100, 110, 120, 130 or 140 mg twice a day, or doses in between.

Alternatively, the compound of formula I may be administered at 20, 30, 40, 50, 60, 70, 80, 100, 120, 140, 160, 180, 200, 220 or 240 mg once a day, or doses in between. The compound of formula I may be administered either continuously or on an alternating schedule, such as 5 days on, 2 days off, or some other schedule as described above.

The combinations of the instant invention may also be co-administered with other well known therapeutic agents that are selected for their particular usefulness against the condition that is being treated. Combinations of the instant invention may alternatively be used sequentially with known pharmaceutically acceptable agent(s) when a multiple combination formulation is inappropriate.

The therapeutic agent(s) can be administered according to therapeutic protocols well known in the art.

It will be apparent to those skilled in the art that the administration of the therapeutic agent(s) can be varied depending on the disease being treated and the known effects of the therapeutic agent(s). Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The invention also relates to a kit, wherein the agents/compounds are disposed in separate containers. The invention also relates to a kit according to any of the foregoing, further comprising integrally thereto or as one or more separate documents, information pertaining to the contents or the kit and the use of the agents/inhibitors. The invention also relates to a kit according to any of the foregoing, wherein the compositions are formulated for reconstitution in a diluent. The invention also relates to a kit according to any of the foregoing, further comprising a container of sterile diluent. The invention also relates to a kit according to any of the foregoing, wherein said compositions are disposed in vials under partial vacuum sealed by a septum and suitable for reconstitution to form a formulation effective for parental administration.

Terminology

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Restenosis" is the renarrowing of an artery or other blood vessel following treatment, such as angioplasty, stent or bypass surgery, for coronary artery disease. Restenosis may also occur in valves after balloon valvuloplasty. Restenosis is less common in stented arteries.

"Stenosis" is the narrowing or constriction of an opening, such as a blood vessel or heart valve. Fat, cholesterol and other substances that accumulate over time may clog the artery. One way to widen a coronary artery is by using balloon angioplasty. Restenosis (renarrowing) of the widened segment occurs in some patients who undergo balloon angioplasty within about six months of the procedure. Restenosed arteries may have to undergo another angioplasty. One way to help prevent restenosis is by using stents. Restenosis is less common in stented arteries. Stenosis can also occur after a coronary artery bypass graft operation. This procedure is done to reroute, or "bypass," blood around clogged arteries. It also improves the supply of blood and oxygen to the heart. In this case, the stenosis may occur in the transplanted blood vessel segments. Like other stenosed arteries, they may need angioplasty or atherectomy to reopen them.

"Therapeutically effective amount" refers to an amount of a compound of the present invention alone or an amount of the combination of compounds claimed or an amount of a compound of the present invention in combination with other active ingredients effective to treat the diseases described herein.

As used in relation to the invention, the term "treating" or "treatment" and the like should be taken broadly. They should not be taken to imply that an animal is treated to total recovery. Accordingly, these terms include amelioration of the symptoms or severity of a particular condition or preventing or otherwise reducing the risk of further development of a particular condition.

It should be appreciated that methods of the invention may be applicable to various species of subjects, preferably mammals, more preferably humans.

As used herein, the compounds of the present invention include the pharmaceutically acceptable derivatives thereof A "pharmaceutically-acceptable derivative" denotes any salt, ester of a compound of this invention, or any other compound which upon administration to a patient is capable of providing (directly or indirectly), such as a prodrug, a compound of this invention, or a metabolite or residue thereof.

The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of the invention. When a basic group and an acid group are present in the same molecule, a compound of the invention may also form internal salts.

The term "prodrug," as used herein, refers to compounds which are rapidly transformed in vivo to the parent compound of the above formula, for example, by hydrolysis in blood. A thorough discussion is provided by T. Higuchi and V. Stella, "Pro-drugs as Novel Delivery systems," Vol. 14 of the A. C. S. Symposium Series, and in Edward B. Roche, ed., "Bioreversible Carriers in Drug Design," American Pharmaceutical Association and Pergamon Press, 1987, both of which are incorporated herein by reference.

The term "coated" with reference to a stent or other implantable medical device is meant to be interpreted broadly to include compounds on the surface or otherwise integral to the device such that the therapeutic compound elutes from the device upon implantation in the subject.

The present invention is described below in examples which are intended to further describe the invention without limitation to its scope.

Example 1

BMS-354825 Inhibits PDGF-Activated Signaling Pathways in VSMCs

To determine if BMS-354825 could inhibit PDGFR activation in VSMCs, we treated serum-starved rat A10 cells with PDGF-BB (5 ng/ml) for 0-30 min in the presence or absence of 50 nM BMS-354825. Cell lysates were analyzed for activation of PDGFRβ, STAT3, Aid, and Erk2 by immunoblotting analyses (FIG. 1A). PDGFRβ is the predominant PDGFR subunit in VSMCs (Raines, 2004) and the only functional PDGFR subunit in A10 cells (Rao et al., 1997). STAT3, Akt, and Erk2 signaling pathways have been reported to mediate PDGF-induced cell migration and proliferation in VSMCs (Graf et al., 1997; Kim et al., 2005; Neeli et al., 2004; Shibata et al., 2003; Vantler et al., 2005; Zhan et al., 2003). PDGF treatment markedly increased PDGFRβ tyrosine phosphorylation, which was detectable at the earliest time point examined (1 min) BMS-354825 (50 nM) effectively blocked PDGF-stimulated PDGFRβ tyrosine phosphorylation at all time points examined FIG. 1A also shows that STAT3, Akt, and Erk2 were activated by PDGF in A10 cells as measured by activation-specific phosphorylation and these were inhibited by BMS-354825.

We next immunoprecipitated PDGFRβ from A10 cells that had been treated with PDGF-BB (5 ng/ml, 5 min) in the presence of 0-25 nM BMS-354825 and then analyzed the PDGFR tyrosine phosphorylation by immunoblotting. As illustrated in FIG. 1B, tyrosine phosphorylation of PDGFR was induced by PDGF stimulation in A10 cells; the response was inhibited by BMS-354825 with an $IC_{50}$ of 3 nM in this assay.

To confirm that BMS-354825 inhibits PDGFR tyrosine kinase activity, PDGFRβ was immunoprecipitated from A10 cells with or without prior PDGF stimulation (5 ng/ml, 5 min). The PDGFR tyrosine kinase activity was determined in vitro in the immune complexes by autophosphorylation in the presence of various concentrations of BMS-354825. As shown in FIG. 1C, BMS-354825 inhibited PDGFR tyrosine kinase activity in a concentration-dependent manner. The 50% inhibition of PDGFRβ phosphorylation was observed at 4 nM BMS-354825.

Example 2

Comparison of PDGFR Inhibition by BMS-354825 and Imatinib

Figure 2:
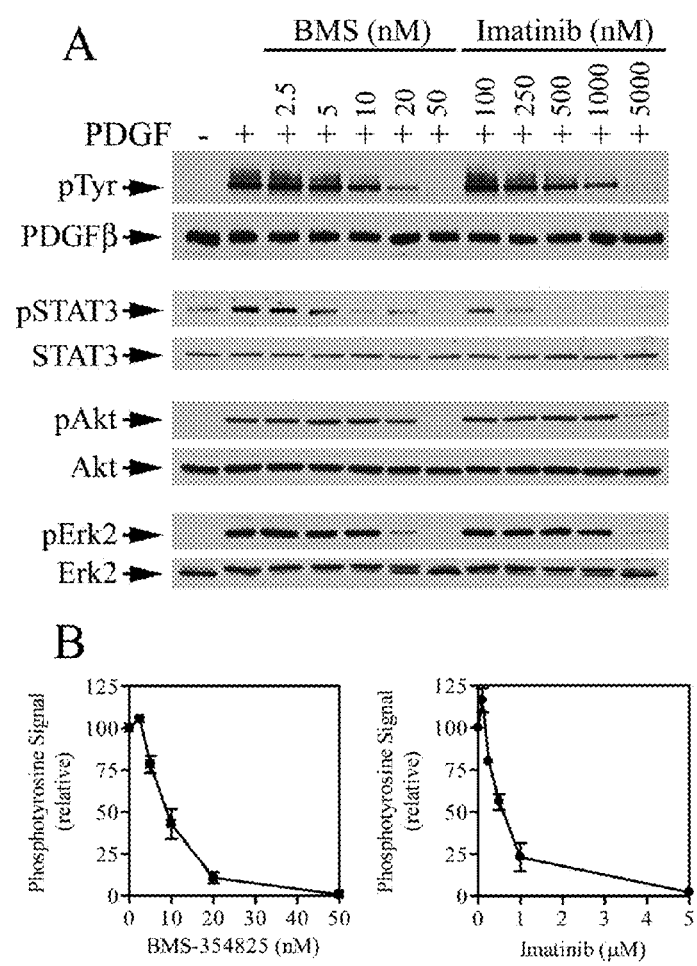
FIG. 2 shows a comparison of the inhibitory effects of BMS-354825 and imatinib in A10 cells. (A) A10 cells were serum-starved, pre-incubated with indicated concentrations of BMS-354825 or imatinib for 20 min, and then stimulated with PDGF-BB (5 ng/ml, 5 min) Cell lysate supernatants were analyzed by immunoblotting similar to that described in FIG. 1A legend. (B) Quantification of PDGFR pTyr signal intensities. Data were from two experiments.

In addition to inhibiting Bcr-Abl and c-Kit, imatinib also inhibits PDGFR tyrosine kinase. To compare the inhibition of PDGFR in VSMCs by BMS-354825 and imatinib, A10 cells were pre-incubated with various concentrations of BMS-354825 or imatinib, stimulated with PDGF-BB, and activation of PDGFR, STAT3, Akt, and Erk2 were analyzed. FIG. 2A shows that PDGF-stimulated PDGFRβ tyrosine phosphorylation was completely blocked by 50 nM BMS-354825. In contrast, 5 μM imatinib was required to achieve the same level of PDGFR inhibition in parallel experiments. Similarly, complete inhibition of PDGF-stimulated Akt and Erk2 activation were observed in cells treated with 50 nM BMS-354825 but only with 5 μM imatinib, whereas decrease in STAT3 tyrosine phosphorylation appeared at lower concentrations of imatinib (FIG. 2A). Of note, inhibition of Akt by both BMS-354825 and imatinib was observed only at the highest drug concentration tested. This may be due to the fact that PDGFR is a strong activator of the phosphoinositide-3 kinase signaling pathway because it binds phosphoinositide-3 kinase directly. Comparison of 50% inhibition of PDGFR tyrosine phosphorylation by BMS-354825 and imatinib in these experiments indicated that BMS-354825 was 67-fold more potent than imatinib in inhibiting PDGFR tyrosine phosphorylation (FIG. 2B).

Example 3

Inhibition of PDGFR in Human AoSMCs by BMS-354825

Figure 3:
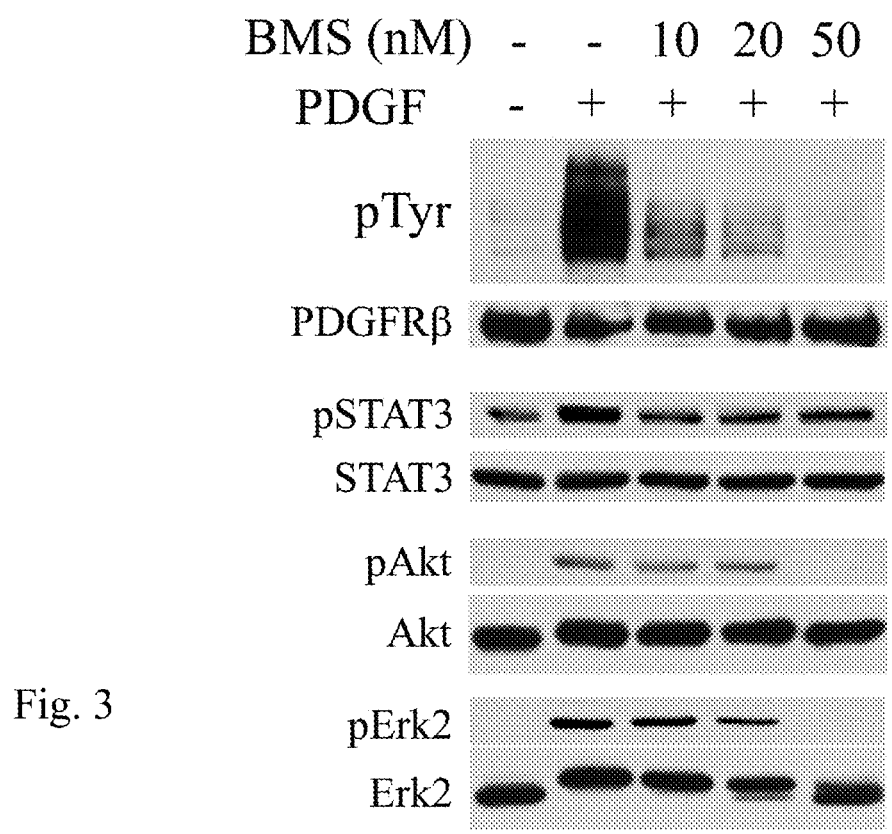
FIG. 3 shows the inhibitory effects of BMS-354825 in primary culture of human AoSMCs. Human AoSMCs were deprived from serum for 18 h, pre-incubated with indicated concentrations of BMS-354825 for 20 min and then stimulated with PDGF-BB (5 ng/ml, 5 min). Cell lysate supernatants were analyzed for activation of PDGFR, STAT3, Akt, and Erk2 by immunoblotting.

To exclude the possibility that the potent inhibition of PDGFR by BMS-354825 is specific to rat VSMCs, we examined the effect of BMS-354825 in primary cultures of human AoSMCs. Human AoSMCs were pre-incubated with 0-50 nM BMS-354825 and then stimulated with PDGF-BB (5 ng/ml, 5 min). PDGFR tyrosine phosphorylation and activation of STAT3, Akt, and Erk2 were analyzed. PDGF markedly induced PDGFR tyrosine phosphorylation in human AoSMCs (FIG. 3). Similar to that observed in A10 cells, the PDGF-stimulated PDGFR tyrosine phosphorylation was completely blocked by 50 nM BMS-354825.

The primary culture of human AoSMCs appeared to have an elevated level of active STAT3 in the absence of PDGF stimulation (FIG. 3). Nevertheless, STAT3 was further activated by PDGF, which was blocked by BMS-354825. BMS-354825, however, was unable to reduce the active STAT3 to a level below the basal activation state in human AoSMCs. Similar to data obtained in A10 cells (FIG. 2), complete inhibition of PDGF-stimulated Akt and Erk2 activation was achieved at 50 nM BMS-354825 in human AoSMCs (FIG. 3).

Inhibition of c-Src Tyrosine Kinase by BMS-354825 in VSMCs.

Figure 4:
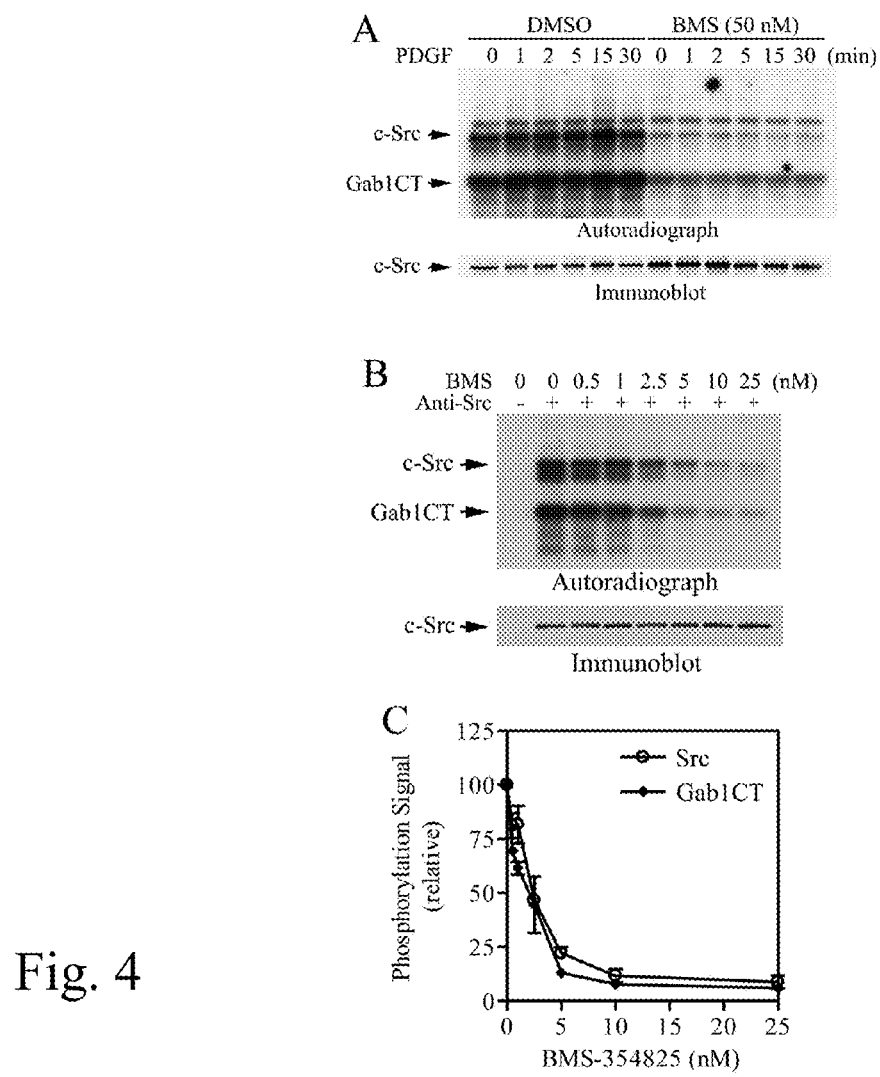
FIG. 4 shows the inhibition of Src tyrosine kinase by BMS-354825. (A) c-Src was immunoprecipitated from serum-starved A10 cells (0) or A10 cells stimulated with PDGF (5 ng/ml) for the indicated time in the presence of absence of 50 nM BMS-354825. Src kinase activity was determined by autophosphorylation and phosphorylation of GST-Gab1CT in the immune complex kinase assay (Ren et al., 2004). After autoradiography, the filter was used for immunoblotting analysis with an anti-Src antibody (lower panel). (B) c-Src was immunoprecipitated from serum-starved A10 cells treated with the indicated concentrations of BMS-354825 for 20 min and Src kinase activity was determined (C) Quantification of radioactive signal from c-Src autophosphorylation and phosphorylation of GST-Gab1CT. The data were from two experiments performed in duplicate (n=4).

To determine if BMS-354825 inhibits c-Src activity in VSMCs, c-Src was immunoprecipitated from serum-starved A10 cells treated with PDGF-BB (5 ng/ml) for 0-30 min in the presence or absence of 50 nM BMS-354825, and the Src tyrosine activity was determined by an immune complex kinase assay using a GST fusion protein of Gab1 fragment as an exogenous substrate (Ren et al., 2004). c-Src isolated from A10 cells without exposure to BMS-354825 and PDGF had detectable kinase activity (FIG. 4A). This kinase activity was reduced to a residual level in c-Src isolated from BMS-354825-treated cells (FIG. 4A). PDGF treatment did not lead to a detectable increase in c-Src kinase activity in A10 cells in repeated experiments. Nevertheless, similar to that observed in unstimulated cells, the activity of c-Src tyrosine kinase in PDGF-stimulated A10 cells was suppressed by BMS-354825 to the residual level (FIG. 4A). This result indicated that c-Src was basally active in A10 cells and that BMS-354825 effectively inhibited the c-Src kinase activity in these cells.

We next treated A10 cells with various concentrations of BMS-354825, immunoprecipitated c-Src and assayed its tyrosine kinase activity to determine the concentration-dependent effect of BMS-354825 on c-Src in A10 cells. FIG. 2B shows that BMS-354825 potently inhibited c-Src tyrosine kinase in A10 cells. The $IC_{50}$ for inhibition of c-Src autophosphorylation was 2.25 nM while the $IC_{50}$ for inhibition the exogenous substrate (GST-Gab1CT) was 2.0 nM.

Example 4

IGF-1R and EGFR in a10 Cells are not Sensitive to BMS-354825 Inhibition

Figure 5:
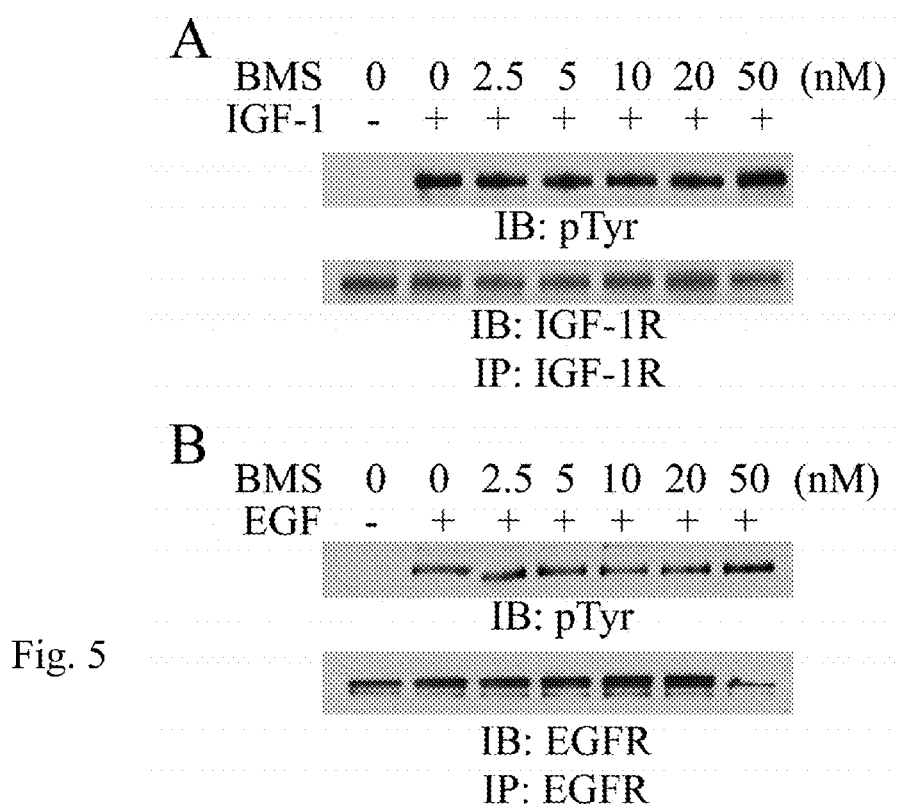
FIG. 5 shows IGF-1R and EGFR are insensitive to BMS-354825. A10 cells were serum-starved, pretreated with indicated concentrations of BMS-354825 (20 min) and then stimulated with IGF-1 (10 ng/ml, 10 min) or EGF (10 ng/ml, 10 min) IGF-1R or EGFR was immunoprecipitated from cell lysate supernatants and analyzed by antibodies to pTyr and IGF-1R (A) or pTyr and EGFR (B).

Besides PDGFR, A10 cells also express IGF-1R and EGFR. To assess if BMS-354825 inhibits other receptor tyrosine kinases in VSMCs, we examined the effects of BMS-354825 on these two receptor tyrosine kinases in A10 cells. As shown in FIG. 5, IGF-1 induced IGF-1R tyrosine phosphorylation, whereas EGF induced EGFR tyrosine phosphorylation in A10 cells. No detectable inhibition of IGF-1R and EGFR tyrosine phosphorylation was observed when A10 cells were treated with up to 50 nM BMS-354825. These data are consistent with a previous report that the $IC_{50s}$ for inhibition of IGF-1R and EGFR by BMS-354825 in the in vitro kinase assays were >5 μM and 180 nM, respectively (Lombardo et al., 2004).

Example 5

BMS-354825 Inhibits PDGF-Stimulated VSMC Migration

Figure 6:
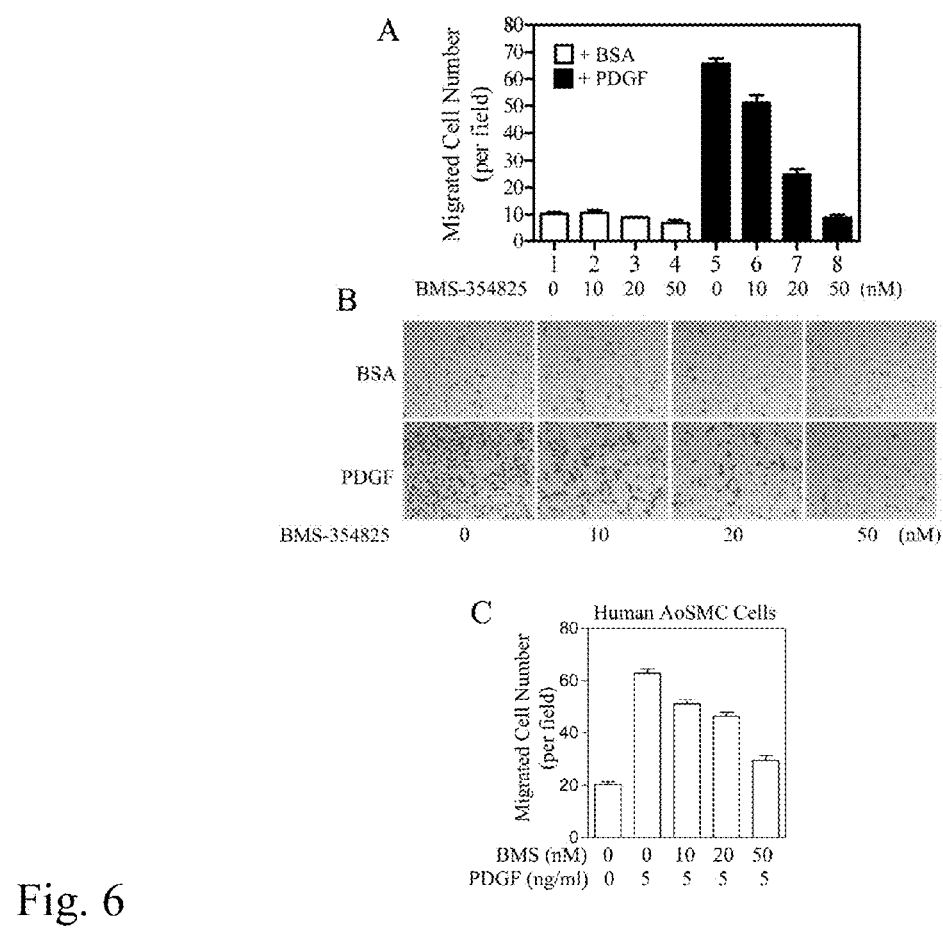
FIG. 6 shows the effect of BMS-354825 on PDGF-stimulated cell migration. Transwell cell migration assay was performed using PDGF-BB (5 ng/ml) as the chemoattractant in the presence or absence of BMS-354825 as indicated. (A) For A10 cells, $1 \times 10^4$ cells were loaded into the upper chamber of each well. Each field was 0.8×0.6 mm. The data were from 2 (lanes 2, 3, 4) to 4 experiments performed in duplicate. (B) Representative views of migrated cells from each sample. Different microscopes were used to acquire data for (A) and (B). Each area in these photos is 1.0×0.8 mm. (C) For human AoSMCs, $0.5 \times 10^4$ cells per well were used. The results were from two experiments performed in duplicate.

Migration of VSMCs plays a critical role in the development of restenosis. PDGF is a potent migratory stimulus for VSMCs. Transwell cell migration assay was performed to determine the effect of BMS-354825 on PDGF-induced VSMCs migration. A10 cells had a low basal migration activity. PDGF (5 ng/ml) stimulated A10 cell migration 7-fold in our assay. This response was inhibited by BMS-354825 in a concentration-dependent manner (FIG. 6A-B). Consistent with the biochemical data, complete inhibition of PDGF-stimulated A10 cells migration was observed at 50 nM BMS-354825.

The primary human AoSMCs had a higher basal migration activity, which is 4 times that of A10 cells. In the presence of PDGF (5 ng/ml), migration of human AoSMCs was increased 3-fold. Again, PDGF-stimulated human AoSMC cell migration was inhibited by BMS-354825 (FIG. 6C).

Example 6

Inhibition of VSMC Proliferation by BMS-354825

Figure 7:
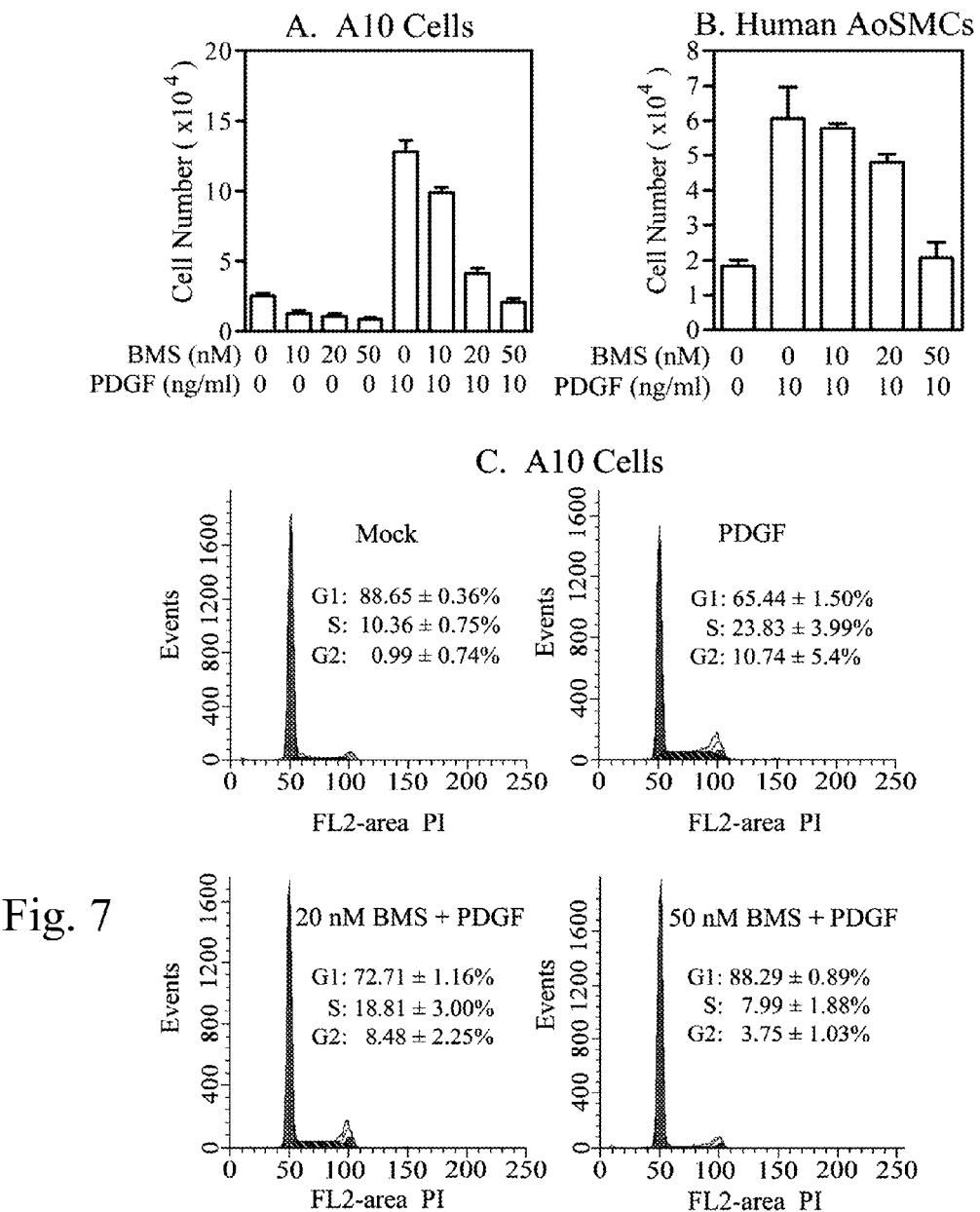
FIG. 7 shows the inhibition of PDGF-stimulated cell proliferation and cell cycle progression by BMS-354825. (A) and (B) A10 cells ($2 \times 10^4$ cells/well) or human AoSMCs ($3.5 \times 10^4$ cells/well) were cultured in DMEM/1% FBS plus indicated PDGF-BB and BMS-354825 for 6 days and viable cell number were determined Data represent two triplicate experiments. (C) A10 cells were incubated with or without PDGF-BB (10 ng/ml) and indicated concentrations of BMS-354825 for 16 h and processed for propidium iodide staining and flow cytometric analysis. The data represent two experiments performed in duplicate. (D) A10 cells ($2 \times 10^4$ cells/well) were cultured in DMEM/1% FBS plus PDGF-BB in the presence of indicated concentrations of BMS-354825 for 6 days. After which, cells were washed and cultured in DMEM/1% FBS plus PDGF-BB with or without BMS-354825 for another 6 days. Viable cell number was determined on Day 12. The data were from three experiments performed in duplicate.
Figure 7:
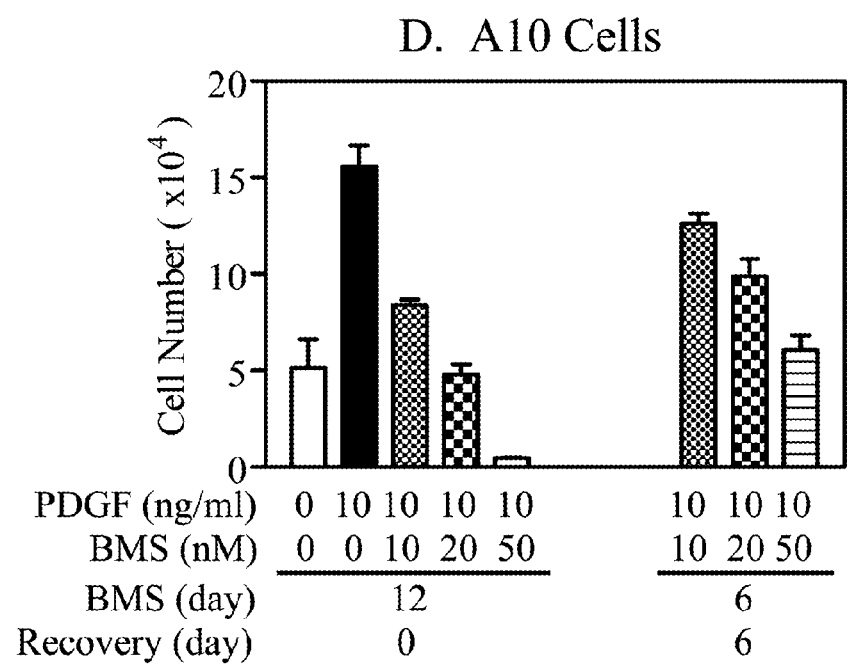

To determine the effect of BMS-354825 on PDGF-stimulated VSMC proliferation, rat A10 cells were incubated in medium containing low serum (1% FBS), PDGF (10 ng/ml), and/or 0-50 nM BMS-354825 for 6 days and viable cell numbers were determined. As shown in FIG. 7A, A10 cell proliferation was stimulated 5-fold by PDGF. BMS-354825 effectively inhibited PDGF-stimulated A10 cell proliferation. Complete inhibition was achieved at 50 nM of BMS-354825. Similar results were obtained in human AoSMCs (FIG. 7B).

We next analyzed the effect of BMS-354825 on PDGF-induced change in cell cycle phase distribution. FIG. 6C shows that PDGF decreased the percentage of cells in G1 phase from 88.65% to 65.44%, while it increased the percentages of cells in S and G2 phases from 10.4% and 0.99% to 23.83% and 10.74%, respectively. The effect of PDGF was suppressed by BMS-354825, such that in the percentages of cells in G1, S, and G2 phases were 88.29%, 7.99% and 3.75% in cells treated with PDGF in the presence of 50 nM BMS-354825 (FIG. 7C).

A previous study showed that the PDGFR specific tyrosine kinase inhibitor AG-1295 could inhibit porcine SMC proliferation and the effect was reversible and not toxic (Banai et al., 1998). To evaluate if the inhibitory effect of BMS-354825 on A10 cell proliferation is reversible, two sets of A10 cells were treated with 0-50 nM BMS-354825 for 6 days. After this time, BMS-354825 was removed from one set of cells and cells were cultured for another 6 days. Viable cell numbers were determined on Day 12. As shown in FIG. 7D, A10 cells proliferation resumed after BMS-354825 withdrawal. Thus, the inhibitory effect of BMS-354825 on A10 cell proliferation was reversible, suggesting that BMS-354825 does not exert a cytotoxic effect on these cells.

Materials and Methods

Antibodies and Reagents:

Antibodies to phosphotyrosine, phospho-Akt, and phospho-Stat3 were from Cell Signaling (Beverly, Mass.). Anti-PDGFRβ (catalog number: 06-498, for immunoblotting) was from Upstate Biotechnology (Lake Placid, N.Y.). Antibodies to PDGFR≈ (catalog number PC-17, for immunoprecipitation) and Src (catalog number OP07, for immune complex kinase assay) were from Calbiochem (San Diego, Calif.). Antibodies to Akt, STAT3, Erk1/2, Src (for immunoblotting), insulin-like growth factor-1 receptor (IGF-1R), and epidermal growth factor receptor (EGFR) were from Santa Cruz Biotechnology (Santa Cruz, Calif.). The anti-activated Erk1/2 antibody was from Promega (Madison, Wis.). PDGF-BB was from PeproTech (Rocky Hill, N.J.). Propidium Iodide (PI) and rat tail type I collagen were from Roche (Indianapolis, Ind.). BMS-354825 (N-(2-chloro-6-methylphenyl)-2-[[6-[4-(2-hydroxyethyl)-1-piperazinyl]-2-methyl-4-pyrimidinyl]amino]-5-thiazolecarboxamide monohydrate) was provided by Bristol-Myers Squibb. Imatinib (Gleevec, STI571) was provided by Novartis.

Cell Culture:

The A10 rat aortic smooth muscle cell line was obtained from American Type Culture Collection (Rockville, Md.) and grown in Dulbecco's modified Eagle's medium (DMEM) supplemented with 10% fetal bovine serum (FBS), 100 units/ml penicillin and 100 μg/ml streptomycin. Primary culture of human aortic smooth muscle cells (AoSMCs) was obtained from Cambrex (Walkersville, Md.) and grown in SmGM-2 Bulletkit® medium (Cambrex) plus 100 units/ml penicillin and 100 μg/ml streptomycin. Human AoSMCs were used before the 7th passage. Cells were maintained at 37° C. in a humidified 95% air and 5% $CO_2$ incubator.

Immunoprecipitation and Immunoblotting:

Cells were lysed in cold lysis buffer [25 mM Tris-HCl (pH 7.2), 150 mM NaCl, 25 mM NaF, 1 mM benzamidine, 1% Triton X-100, 1 mM $Na_3VO_4$, 20 mM p-nitrophenyl phosphate, 2 μg/ml leupeptin, 2 μg/ml aprotinin, 100 μg/ml phenylmethylsulfonyl fluoride]. Cell lysate supernatants were obtained by microcentrifugation at 4° C. for 15 min and the protein concentration was determined. For immunoblotting analysis of cell lysates, cell lysate supernatants were heat-denatured in SDS loading buffer. Antibodies to activated STAT3, activated Akt, activated Erk1/2, and phosphotyrosine were used to assess the activation of these molecules and receptor tyrosine kinases by immunoblotting. Immunoblotting was performed essentially as described previously (Cunnick et al., 2001; Cunnick et al., 2002; Ren and Wu, 2003) using the SuperSignal West Pico Chemiluminescent reagent (Pierce, Rockford, Ill.). Each immunoprecipitation was performed using 600 μg of cell lysate supernatant, 2 μg of specific antibody indicated in the figure legends and 30 μl of Protein-A or Protein-G at 4° C. for 2 h. Immune complex was collected by microcentrifugation and washed three times with the lysis buffer. Quantification of immunoreactive band intensity was achieved using the ImageQuant program (Molecular Dynamics).

Protein Tyrosine Kinase Assays:

PDGFR was immunoprecipitated with an anti-PDGFR antibody (Calbiochem, PC17). Immunoprecipitates were washed twice with the lysis buffer and twice with kinase buffer [50 mM HEPES (pH 7.4), 10 mM $MnCl_2$, 0.1 mM $Na_3VO_4$]. The immune complex kinase assay was performed in 50 μl reaction mixture [kinase buffer plus 20 μCi [γ-$^{32}$P]-ATP, 10 μM ATP] at 30° C. for 15 min. Kinase reaction was terminated by addition of 17 μl of 4×SDS loading buffer and heat-denaturation at 95° C. for 10 min. Samples were subjected to 8% SDF-polyacrylamide gel electrophoresis, transferred to nitrocellulose membrane. Phosphorylation was quantified by phosphoimage analysis or autoradiography. The immune complex kinase assay for c-Src was performed as described previously (Ren et al., 2004).

Cell Migration Assay:

Cell migration was measured using the Transwell cell migration assay (Ren et al., 2004). Transwell cell culture insert polycarbonate membrane (6.5 mm, 8.0 μm pore size, Costar, Corning, N.Y.) was coated with rat tail type I collagen (10 μg/ml in PBS) at 4° C. for 18 h and air-dried. VSMCs (80% confluent) were serum-starved in DMEM/0.1% BSA for 18 h, detached from plates by digestion with 1:3 diluted trypsin-EDTA (Invitrogen), washed with DMEM, and resuspended in DMEM/0.1% BSA at $5 \times 10^4$ cells/ml for A10 cells or $2.5 \times 10^4$ cells/ml for human AoSMCs. Cell suspension (0.2 ml per well) was incubated with BMS-354825 or solvent (DMSO) in 1.5-ml microfuge tube for 20 min before been placed in the upper chamber of Transwell. The lower chamber contained 0.6 ml DMEM/0.1% BSA with or without 5 ng/ml PDGF-BB (PeroTech, Rocky Hill, N.J.) and BMS-354825. After incubation at 37° C./5% $CO_2$ for 4 h, cells remaining on the upper membrane surface were mechanically removed with a cotton swab. Migrated cells on the lower side of membrane were fixed and stained with the HEMA3 reagents (Fisher Scientific, Swanee, Ga.) and enumerated under a microscope in eight randomly chosen fields with 10×10 lens. Each field for quantification of the migrated cell number has an area of 0.8×0.6 mm.

Cell Proliferation Analysis:

A10 cells and human AoSMC cells were seeded in triplicate at $2\times10^4$ per plate in 6-cm plates in DEME/1% FBS with or without PDGF-BB (10 ng/ml). After 24 h (Day 0), cells were treated with DMSO (solvent) or 10-50 nM BMS-354825. Medium was changed on Day 3. Viable cell number was determined on Day 6 as described (Dorsey et al., 2000). For the recovery experiment, cells were treated as above for 6 days and then cultured without BMS-354825 for another 6 days.

Flow Cytometric Analysis:

A10 cells (80% confluent) were serum starved in DMEM/0.1% BSA for 24 h. After which, PDGF-BB (10 ng/ml) and BMS-354825 or DMSO was added and the incubation was continued for another 16 h. Cells were collected by trypsinization and resuspended in PBS at $5\times10^6$ cells/ml. Cells were fixed in cold 70% ethanol, washed with PBS, and incubated with propidium iodide (20 µg/ml) and RNase (200 µg/ml) for 1 h at room temperature at a cell concentration of $1\times10^6$ cells/ml. Flow cytometric analysis of cell cycle phase distribution was performed using a Becton Dickinson FACSCalibur flow cytometer (Becton Dickinson, San Jose, Calif.) and $1\times10^4$ events were recorded for each sample.

REFERENCES

Bailey S R (2002) Coronary restenosis: a review of current insights and therapies. *Catheter Cardiovasc Interv* 55:265-271.

Banai S, Wolf Y, Golomb G, Pearle A, Waltenberger J, Fishbein I, Schneider A, Gazit A, Perez L, Huber R, Lazarovichi G, Rabinovich L, Levitzki A and Gertz S D (1998) PDGF-receptor tyrosine kinase blocker AG1295 selectively attenuates smooth muscle cell growth in vitro and reduces neointimal formation after balloon angioplasty in swine. *Circulation* 97:1960-1969.

Bowman T, Broome M A, Sinibaldi D, Wharton W, Pledger W J, Sedivy J M, Irby R, Yeatman T, Courtneidge S A and Jove R (2001) Stat3-mediated Myc expression is required for Src transformation and PDGF-induced mitogenesis. *Proc Natl Acad Sci USA* 98:7319-7324.

Buchdunger E, Zimmermann J, Mett H, Meyer T, Muller M, Druker B J and Lydon N B (1996) Inhibition of the Abl protein-tyrosine kinase in vitro and in vivo by a 2-phenylaminopyrimidine derivative. *Cancer Res* 56:100-104.

Burgess M R, Skaggs B J, Shah N P, Lee F Y and Sawyers C L (2005) Comparative analysis of two clinically active BCR-ABL kinase inhibitors reveals the role of conformation-specific binding in resistance. *Proc Natl Acad Sci USA* 102:3395-3400.

Cunnick J M, Mei L, Doupnik C A and Wu J (2001) Phosphotyrosines 627 and 659 of Gab1 constitute a bisphosphoryl tyrosine-based activation motif (BTAM) conferring binding and activation of SHP2. *J Biol Chem* 276:24380-24387.

Cunnick J M, Meng S, Ren Y, Desponts C, Wang H G, Djeu J Y and Wu J (2002) Regulation of the mitogen-activated protein kinase signaling pathway by SHP2. *J Biol Chem* 277:9498-9504.

Dangas G and Kuepper F (2002) Cardiology patient page. Restenosis: repeat narrowing of a coronary artery: prevention and treatment. *Circulation* 105:2586-2587.

Deininger M, Buchdunger E and Druker B J (2005) The development of imatinib as a therapeutic agent for chronic myeloid leukemia. *Blood* 105:2640-2653.

Dorsey J F, Jove R, Kraker A J and Wu J (2000) The pyrido[2,3-d]pyrimidine derivative PD180970 inhibits p210Bcr-Abl tyrosine kinase and induces apoptosis of K562 leukemic cells. *Cancer Res* 60:3127-3131.

Druker B J, Tamura S, Buchdunger E, Ohno S, Segal G M, Fanning S, Zimmermann J and Lydon N B (1996) Effects of a selective inhibitor of the Abl tyrosine kinase on the growth of Bcr-Abl positive cells. *Nat Med* 2:561-566.

Ferns G A, Raines E W, Sprugel K H, Motani A S, Reidy M A and Ross R (1991) Inhibition of neointimal smooth muscle accumulation after angioplasty by an antibody to PDGF. *Science* 253:1129-1132.

Fishbein I, Waltenberger J, Banai S, Rabinovich L, Chorny M, Levitzki A, Gazit A, Huber R, Mayr U, Gertz S D and Golomb G (2000) Local delivery of platelet-derived growth factor receptor-specific tyrphostin inhibits neointimal formation in rats. *Arterioscler Thromb Vasc Biol* 20:667-676.

Graf K, Xi X P, Yang D, Fleck E, Hsuch W A and Law RE (1997) Mitogen-activated protein kinase activation is involved in platelet-derived growth factor-directed migration by vascular smooth muscle cells. *Hypertension* 29:334-339.

Heldin C H and Westermark B (1999) Mechanism of action and in vivo role of platelet-derived growth factor. *Physiol Rev* 79:1283-1316.

Huron D R, Gorre M E, Kraker A J, Sawyers C L, Rosen N and Moasser M M (2003) A novel pyridopyrimidine inhibitor of abl kinase is a picomolar inhibitor of Bcr-abl-driven K562 cells and is effective against STI571-resistant Bcr-abl mutants. *Clin Cancer Res* 9:1267-1273.

Kim J H, Jin Y R, Park B S, Kim T J, Kim S Y, Lim Y, Hong J T, Yoo H S and Yun Y P (2005) Luteolin prevents PDGF-BB-induced proliferation of vascular smooth muscle cells by inhibition of PDGF beta-receptor phosphorylation. *Biochem Pharmacol* 69:1715-1721.

Lahaye T, Riehm B, Berger U, Paschka P, Muller M C, Kreil S, Merx K, Schwindel U, Schoch C, Hehlmann R and Hochhaus A (2005) Response and resistance in 300 patients with BCR-ABL-positive leukemias treated with imatinib in a single center: a 4.5-year follow-up. *Cancer* 103:1659-1669.

Levitzki A (2005) PDGF receptor kinase inhibitors for the treatment of restenosis. *Cardiovasc Res* 65:581-586.

Logrono R, Jones D V, Faruqi S and Bhutani M S (2004) Recent advances in cell biology, diagnosis, and therapy of gastrointestinal stromal tumor (GIST). *Cancer Biol Ther* 3:251-258.

Lombardo L J, Lee F Y, Chen P, Norris D, Barrish J C, Behnia K, Castaneda S, Cornelius L A, Das J, Doweyko A M, Fairchild C, Hunt J T, Inigo I, Johnston K, Kamath A, Kan D, Klei H, Marathe P, Pang S, Peterson R, Pitt S, Schieven G L, Schmidt R J, Tokarski J, Wen M L, Wityak J and Borzilleri R M (2004) Discovery of N-(2-chloro-6-methylphenyl)-2-(6-(4-(2-hydroxyethyl)-piperazin-1-yl)-2-methylpyrimidin-4-ylamino)thiazole-5-carboxamide (BMS-354825), a dual Src/Abl kinase inhibitor with potent antitumor activity in preclinical assays. *J Med Chem* 47:6658-6661.

Michaels A D and Chatterjee K (2002) Cardiology patient pages. Angioplasty versus bypass surgery for coronary artery disease. *Circulation* 106:e187-190.

Myllarniemi M, Frosen J, Calderon Ramirez L G, Buchdunger E, Lemstrom K and Hayry P (1999) Selective tyrosine kinase inhibitor for the platelet-derived growth factor receptor in vitro inhibits smooth muscle cell proliferation after reinjury of arterial intima in vivo. *Cardiovasc Drugs Ther* 13:159-168.

Neeli I, Liu Z, Dronadula N, Ma Z A and Rao G N (2004) An essential role of the Jak-2/STAT-3/cytosolic phospholipase A(2) axis in platelet-derived growth factor BB-induced vascular smooth muscle cell motility. *J Biol Chem* 279: 46122-46128.

O'Hare T, Walters D K, Stoffregen E P, Jia T, Manley P W, Mestan J, Cowan-Jacob S W, Lee F Y, Heinrich M C, Deininger M W and Druker B J (2005) In vitro activity of Bcr-Abl inhibitors AMN107 and BMS-354825 against clinically relevant imatinib-resistant Abl kinase domain mutants. *Cancer Res* 65:4500-4505.

Pompili V J, Gordon D, San H, Yang Z, Muller D W, Nabel G J and Nabel E G (1995) Expression and function of a recombinant PDGF B gene in porcine arteries. *Arterioscler Thromb Vasc Biol* 15:2254-2264.

Raines E W (2004) PDGF and cardiovascular disease. *Cytokine Growth Factor Rev* 15:237-254.

Rao R S, Miano J M, Olson E N and Seidel C L (1997) The A10 cell line: a model for neonatal, neointimal, or differentiated vascular smooth muscle cells? *Cardiovasc Res* 36:118-126.

Ren Y, Meng S, Mei L, Zhao Z J, Jove R and Wu J (2004) Roles of Gab1 and SHP2 in paxillin tyrosine dephosphorylation and Src activation in response to epidermal growth factor. *J Biol Chem* 279:8497-8505.

Ren Y and Wu J (2003) Simultaneous suppression of Erk and Akt/PKB activation by a Gab1 pleckstrin homology (PH) domain decoy. *Anticancer Res* 23:3231-3236.

Sanz-Gonzalez S M, Castro C, Perez P and Andres V (2004) Role of E2F and ERK1/2 in STI571-mediated smooth muscle cell growth arrest and cyclin A transcriptional repression. *Biochem Biophys Res Commun* 317:972-979.

Shah N P, Tran C, Lee F Y, Chen P, Norris D and Sawyers C L (2004) Overriding imatinib resistance with a novel ABL kinase inhibitor. *Science* 305:399-401.

Shibata R, Kai H, Seki Y, Kato S, Wada Y, Hanakawa Y, Hashimoto K, Yoshimura A and Imaizumi T (2003) Inhibition of STAT3 prevents neointima formation by inhibiting proliferation and promoting apoptosis of neointimal smooth muscle cells. *Hum Gene Ther* 14:601-610.

Sihvola R K, Tikkanen J M, Krebs R, Aaltola E M, Buchdunger E, Laitinen O, Koskinen P K and Lemstrom K B (2003) Platelet-derived growth factor receptor inhibition reduces allograft arteriosclerosis of heart and aorta in cholesterol-fed rabbits. *Transplantation* 75:334-339.

Sirois M G, Simons M and Edelman E R (1997) Antisense oligonucleotide inhibition of PDGFR-beta receptor subunit expression directs suppression of intimal thickening. *Circulation* 95:669-676.

Vantler M, Caglayan E, Zimmermann W H, Baumer A T and Rosenkranz S (2005) Systematic evaluation of anti-apoptotic growth factor signaling in vascular smooth muscle cells. Only phosphatidylinositol 3'-kinase is important. *J Biol Chem* 280:14168-14176.

Wang Y Z, Wharton W, Garcia R, Kraker A, Jove R and Pledger W J (2000) Activation of Stat3 preassembled with platelet-derived growth factor beta receptors requires Src kinase activity. *Oncogene* 19:2075-2085.

Wisniewski D, Lambek C L, Liu C, Strife A, Veach D R, Nagar B, Young M A, Schindler T, Bornmann W G, Bertino J R, Kuriyan J and Clarkson B (2002) Characterization of potent inhibitors of the Bcr-Abl and the c-kit receptor tyrosine kinases. *Cancer Res* 62:4244-4255.

Zhan Y, Kim S, Izumi Y, Izumiya Y, Nakao T, Miyazaki H and Iwao H (2003) Role of JNK, p38, and ERK in platelet-derived growth factor-induced vascular proliferation, migration, and gene expression. *Arterioscler Thromb Vasc Biol* 23:795-801.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of treating restenosis or stenosis in a patient comprising administering to a patient in need of such treatment a composition comprising:
   dasatinib or a pharmaceutically acceptable derivative thereof in an amount effective to treat restenosis or stenosis.

2. The method according to claim 1, wherein the effective amount ranges between about 35 mg and about 150 mg dasatinib per patient per day.

3. The method according to claim 1, wherein the effective amount ranges between about 35 mg and about 140 mg dasatinib per patient per day.

4. The method according to claim 1, wherein the effective amount ranges between about 70 mg and about 140 mg dasatinib per patient per day.

5. The method according to claim 1, wherein the dasatinib is administered orally.

6. The method according to claim 5, further comprising administering at least one additional therapeutic agent selected from the group consisting of antiplatelet agents, antimigratory agents, antifibrotic agents, antiproliferatives, antiinflammatories and combinations thereof.

7. The method according to claim 1, further comprising administering to the patient one or more compounds that inhibit inflammation or smooth muscle cell proliferation.

8. The method according to claim 1, further comprising administering to the patient one or more additional therapeutic agents.

9. The method according to claim 8, wherein the one or more additional therapeutic agents is selected from the group consisting of sirolimus and paclitaxel, and wherein the composition is administered locally as a drug eluting stent.

10. A method of treating an artery obstructive disease in a patient comprising administering between about 10 mg and about 250 mg of dasatinib per day to the patient;
    wherein the artery obstructive disease is restenosis or stenosis.

11. The method of claim 10, wherein the dasatinib is administered between about 35 mg per day to about 140 mg per day or between about 70 mg per day to about 140 mg per day.

12. The method of claim 11, wherein the dasatinib is administered once a day, twice a day, or orally twice a day.

13. The method of claim 10, wherein the dasatinib is administered orally, parenterally, intravenously, intramuscularly, intraperitoneally, subcutaneously, rectally, topically, or via a coated implanted device.

14. The method of claim 13, wherein the coated implanted device is a stent.

15. The method of claim 13, the dasatinib is administered between 15 mg and 200 mg twice a day, between 30 mg and 100 mg twice a day, between 70 mg and 150 mg twice a day, 70 mg twice a day, between 50 mg and 300 mg once a day, between 140 mg and 250 mg once a day, or between 100 mg and 200 mg once a day.

16. The method of claim 10, wherein the dasatinib is administered once a day for 2 to 10 days, once a day for 3 to 9 days, once a day for 4 to 8 days, once a day for 5 days, once a day for 3 days to 5 weeks, once a day for 4 days to 4 weeks, once a day for 5 days to 3 weeks, or once a day for 1 week to 2 weeks.

17. The method of claim 10, wherein the dasatinib is administered at 0.1 to 2 mg/kg of body weight of active compound per day, or at 0.1 to 2 mg/kg of body weight of active compound per day.

18. The method of claim 10, further comprising administering sirolimus or paclitaxel with the dasatinib.

19. The method of claim 18, wherein the dasatinib and sirolimus or paclitaxel are administered as a sirolimus and dasatinib-eluting stent or a paclitaxel and dasatinib-eluting stent.

\* \* \* \* \*